(12) United States Patent
Lee

(10) Patent No.: US 11,993,656 B2
(45) Date of Patent: May 28, 2024

(54) METHOD OF TREATING IgG4-RELATED DISEASE

(71) Applicant: Jason Kihyuk Lee, Toronto (CA)

(72) Inventor: Jason Kihyuk Lee, Toronto (CA)

( * ) Notice: Subject to any disclaimer, the term of this patent is extended or adjusted under 35 U.S.C. 154(b) by 193 days.

(21) Appl. No.: 17/162,934

(22) Filed: Jan. 29, 2021

(65) Prior Publication Data

US 2021/0238293 A1     Aug. 5, 2021

Related U.S. Application Data

(60) Provisional application No. 62/968,335, filed on Jan. 31, 2020.

(51) Int. Cl.
| | |
|---|---|
| *A61K 39/395* | (2006.01) |
| *A61K 9/00* | (2006.01) |
| *A61K 38/20* | (2006.01) |
| *C07K 16/28* | (2006.01) |

(52) U.S. Cl.
CPC ........ *C07K 16/2866* (2013.01); *A61K 9/0019* (2013.01); *A61K 9/0053* (2013.01); *A61K 38/2026* (2013.01); *A61K 39/395* (2013.01)

(58) Field of Classification Search
None
See application file for complete search history.

(56) References Cited

PUBLICATIONS

Shirley (2017, Drugs 77:1115-1121).*
Zen et al. (2007, Hepatology 45:1538-1546).*
Pieringer et al., 2014, Orphanet J Rare Diseases 9(110): pp. 1-14.*
Gandhi et al., 2017, Exp Rev Clin Immunol 13(4): 425-437.*
Simpson, Rachel S. et al., "Dupilumab as a novel steroid-sparing treatment for IgG4-related disease", Ann Rheum Dis: doi:10.1136/annrheumdis-2019-216368, Dec. 19, 2019.

* cited by examiner

*Primary Examiner* — Elizabeth C. Kemmerer
(74) *Attorney, Agent, or Firm* — Smart & Biggar LP

(57) ABSTRACT

This patent relates to a method of treating IgG4-related disease comprising administration of an Interleukin-4 inhibitor/antagonist, an IL-4 receptor alpha inhibitor, or a compound which blocks assembly of IL-4 receptor alpha with IL-13 receptor alpha. The method of treating IgG4-related disease may comprise administration of a JAK inhibitor. The method of treating IgG4-related disease may comprise administration of duplimab and/or pitrakinra.

5 Claims, 2 Drawing Sheets

METHOD OF TREATING IgG4-RELATED DISEASE

FIELD OF THE INVENTION

The invention relates to IgG4-Related Disease, and treatment thereof.

BACKGROUND OF THE INVENTION

IgG4-related disease (IgG4-RD) is a rare fibroinflammatory, multi-systemic condition with a relapsing-remitting progression (Kamisawa et al., The Lancet 2015:385:1460-71, incorporated herein by reference). The level of serum IgG4 correlates with inflammatory activity and organ involvement. Glucocorticoids are first-line for IgG4-RD, but there are numerous adverse effects with chronic use (Shirakashi et al., Sci Rep 2018: 8(1):10262, incorporated herein by reference).

Second-line treatments are chemotherapeutic immunosuppressants, and the third-line treatment is B-cell depleting rituximab, an anti-CD20 monoclonal antibody. The adverse effects associated with these therapies include increased risks of infection and potentially lasting immune deficiency (Kaplan et al., J Allergy Clin Immunol Pract 2014:2(5):594-600, incorporated herein by reference).

Although immunosuppressants aim to potentially mitigate such concerns, currently, there is no existing biologic treatment which is approved to control IgG4-RD as a steroid-sparing agent that has a low risk for potential long-term adverse effects.

IL-4 Inhibitors and IL-4+IL-13 Inhibitors

Interleukin-4 (IL-4) is a pleiotropic cytokine produced mostly by mast cells, basophils, a subset of activated T cells, eosinophils and neutrophils. Its actions are generally antagonistic to those of Interferon gamma. Interleukin 13 (IL-13) is primarily produced by Th2 cells, but is also secreted by other T helper cell subsets CD8+ T cells, mast cells, eosinophils and basophils following activation; it induces proliferation and Immunoglobulin E synthesis by human B cells, inhibits production of proinflammatory cytokines and chemokines by monocytes/macrophages, and has important anti-inflammatory properties.

IL-4 and IL-13 bind to heterodimer complex receptors. IL-13 binds to the cytokine receptor composed of subunits IL-13 receptor-alpha (IL-13Rα) and IL-4 receptor-alpha (IL-4Rα) to initiate the activation of multiple transduction pathways including tyrosine kinase 2 and Janus kinase. IL-4 binds to the cytokine receptor composed of IL-4Ra and the common gamma chain (gamma c). There is also a known interaction with SHC-transforming protein 1.

Dupilumab is a human monoclonal antibody that inhibits IL-4 and IL-13 signaling by specifically binding to the IL-4Rα subunit that is shared between the IL-4 and IL-13 receptor complexes. Dupilumab inhibits IL-4 signaling via the Type I receptor (IL-4Rα/γc) and both IL-4 and IL-13 signalling through the Type II receptor (IL-4Rα/IL-13Rα). Amongst the many functions, IL-4 causes isotype-switching from IgM to IgG4 (along with all other subclasses of IgG and isotypes) and IL-13 is implicated in tissue fibrosis (Gandhi et al., Expert Review of Clinical Immunology, vol. 13 no. 5, 2017 pp. 425-437, incorporated herein by reference). Dupilumab is indicated for the treatment of moderate to severe atopic dermatitis in adult patients who are candidates for chronic systemic therapy as well as moderate to severe asthma and nasal polyposis by the FDA. It is postulated that by inhibiting IL-13 and IL-4 through Dupilumab, GATA3 transcription factor function (amongst many others) is down regulated. Dupilumab is not currently indicated for episodic use. Dupilumab has been observed to be safe with long-term use across multiple indications (Blauvelt et al., The Lancet 2017: 389(10086):2287-2303, incorporated herein by reference).

SUMMARY OF THE INVENTION

According to one aspect of the invention is provided a method of treating IgG4-Related Disease in a patient in need thereof comprising administering an effective amount of a compound selected from a Interleukin-4 inhibitor/antagonist, an IL-4 receptor alpha (IL-4RA) inhibitor, and a compound which blocks assembly and/or function of IL-4RA with IL-13 receptor alpha.

In a further aspect of the invention is provided the use of a compound selected from a Interleukin-4 inhibitor/antagonist, an IL-4 receptor alpha (IL-4RA) inhibitor, and a compound which blocks assembly of IL-4RA with IL-13 receptor alpha for treatment of IgG4-Related Disease.

According to certain embodiments, the compound may also be a JAK inhibitor.

According to certain embodiments, the compound may also be an IL-13 inhibitor or is combined with an IL-13 inhibitor.

According to certain embodiments, the compound is dupilumab.

According to certain embodiments, the IL-4Ra inhibitor is pitrakinra.

According to certain embodiments, the IL-4Ra inhibitor is a combined IL-4 and IL-13 inhibitor.

According to certain embodiments, the administration is via subcutaneous injection.

According to certain embodiments, the administration is a parenteral administration.

According to certain embodiments, the administration is oral.

According to certain embodiments, the effective amount is an initial dose of 600 mg followed by a 300 mg dose every other week.

According to certain embodiments, the effective amount is an initial dose of 400 mg followed by a 200 mg dose every other week.

According to a certain aspect of the invention is described a method of treating IgG4-RD in a patient in need thereof, comprising administration of an effective amount of dupilumab to said patient.

According to a certain aspect of the invention is described a method of treating IgG4-RD in a patient in need thereof, comprising administration of an effective amount of medication to inhibit the action of IL-4 and IL-13 as aforementioned.

DESCRIPTION

Figure 1A:
FIG. 1a shows a patient's pre-treatment MRI, showing extensive retroperitoneal and extraperitoneal fibrosis.

Unless defined otherwise, all technical and scientific terms used herein have the same meaning as commonly understood by one of ordinary skill in the art to which this invention belongs.

As used herein, the term "about," when used in reference to a particular recited numerical value, means that the value may vary from the recited value by no more than 10%.

As used in this patent application, a "subject" or "patient" may generally be any human or non-human animal that would benefit from the methods described in this application, such as a subject or patient afflicted with IgG4-RD. In one embodiment, a subject is a human subject.

As used in this patent application, unless the context makes clear otherwise, "treatment," and similar word such as "treated," "treating" etc., is an approach for obtaining beneficial or desired results, including and preferably clinical results. Treatment can involve optionally either the amelioration of symptoms of the disease or condition, the delaying of the progression of the disease or condition, or curing the disease or condition.

The compositions and compounds of the present invention may be administered by one or more administration routes using one or more of the various methods known in the art. As will be apparent to those skilled in the art, the route and/or mode of administration will vary depending upon the desired results and/or the formulation of the composition or compound. Suitable routes of administration include, but are not limited to, intravenous, intramuscular, intradermal, intraperitoneal, subcutaneous, spinal or other parenteral routes of administration, for example by injection or infusion. As used herein, the term "parenteral administration" refers to modes of administration other than through the intestinal route, and includes intravenous, intramuscular, intraarterial, intrathecal abdominal, intracapsular, intraorbital, intracardiac intradermal, intraperitoneal, transtracheal, subcutaneous, subepidermal, intraarticular, subcapsular, intrathecal, intraspinal, epidural and intrasternal injections and infusions. Routes of administration may also include topically, such as across epithelia, or by mucosal administration routes, for example, intranasally, intraorally, intravaginal, intrarectal, or sublingual. The composition or compound may also be administered orally.

The compounds or compositions for use described above are prepared into dosage forms suited for the active ingredients. Such dosage forms include, for example, tablets, pills, pellets, lozenges, troches, capsules, suppositories, liniments, lotions, ointments, pastes, sprays, inhalants, suspensions, mixtures, gels, emulsions, tinctures, and the like.

The compounds and compositions of the invention may be formulated with suitable carriers, excipients, coloring agents, flavoring agents, and the like, and other agents that provide suitable transfer, delivery, tolerance, and the like.

In certain embodiments, the compound or composition of the present invention may comprise an antibody. Various delivery systems are known that can be used to administer these compounds or compositions, e.g., encapsulation in liposomes, microparticles, microcapsules, and receptor mediated endocytosis. Methods of administration for these compounds and compositions include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

It will be apparent to one of skill in the art when a compound of the invention can exist as a salt form, especially as an acid addition salt or a base addition salt. When a compound can exist in a salt form, such salt forms are included within the scope of the invention. Pharmaceutically acceptable salts include, when appropriate, pharmaceutically acceptable base addition salts and acid addition salts, e.g., metal salts, such as alkali and alkaline earth metal salts; ammonium salts; organic amine addition salts; amino acid addition salts; and sulfonate salts. Acid addition salts include inorganic acid addition, salts such as hydrochloride, sulfate and phosphate; and organic acid addition salts, such as alkyl sulfonate, arylsulfonate, acetate, maleate, fumarate, tartrate, citrate and lactate. Examples of metal salts are alkali metal salts, such as lithium salt, sodium salt and potassium salt; alkaline earth metal salts, such as magnesium salt and calcium salt, aluminum salt and zinc salt. Examples of ammonium salts are ammonium salt and tetramethylammonium salt. Examples of organic amine addition salts are salts with morpholine and piperidine. Examples of amino acid addition salts are salts with glycine, phenylalanine, glutamic acid and lysine. Sulfonate salts include mesylate, tosylate and benzene sulfonic acid salts.

The term "pharmaceutically acceptable" generally that the agent does no harm to the subject, and preferably has been approved by a national regulatory agency, or listed in the U.S. Pharmacopeia, European Pharmacopeia or other generally recognized Pharmacopeia for use in animals, and more particularly in humans.

IgG4-RD is a tumefactive fibroinflammatory lesion that is histologically characterized by dense inflammation, including blood vessels, accompanied by fibrosis. Patients with IgG4-RD have elevated levels of IgG4-positive plasma cells in the tissues. This may or may not be associated with an increase in serum IgG4 levels. Recent medical literature suggests that IgG4-RD can involve almost any organ. Diseases including autoimmune pancreatitis, Mikulicz's syndrome (lacrimal and salivary gland), Kuttner's tumor (submandibular salivary gland), Riedel's thyroiditis, and retroperitoneal fibrosis (Ormond's disease), which have been identified as unique medical conditions in the past, are now considered part of the spectrum of IgG4-RD.

Consequently, in the present application, IgG4-RD includes, but is not limited to, IgG4-related sialadenitis (chronic sclerosing sialadenitis, Küttner's tumour, Mikulicz's disease), IgG4-related dacryoadenitis (Mikulicz's disease), IgG4-related ophthalmic disease (idiopathic orbital inflammatory disease, orbital pseudotumor), chronic sinusitis, eosinophilic angiocentric fibrosis, IgG4-related hypophysitis (IgG4-related panhypophysitis, IgG4-related adenohypophysitis, gG4-related infundibuloneurohypophysitis, autoimmune hypophysitis), IgG4-related pachymeningitis, IgG4-related leptomeningitis (idiopathic hypertrophic pachymeningitis), IgG4-related pancreatitis (Type 1 autoimmune pancreatitis, IgG4-related AIP, lymphoplasmacytic sclerosing pancreatitis, chronic pancreatitis with diffuse irregular narrowing of the main pancreatic duct), IgG4-related lung disease (Pulmonary inflammatory pseudotumour), IgG4-related pleuritis, IgG4-related hepatopathy, IgG4-related sclerosing cholangitis, IgG4-related cholecystitis, IgG4-related aortitis (inflammatory aortic aneurysm), IgG4-related periaortitis (chronic periaortitis), IgG4-related periarteritis, IgG4-related pericarditis, IgG4-related mediastinitis (fibrosing mediastinitis), IgG4-related retroperitoneal fibrosis (retroperitoneal fibrosis, Albarran-Ormond syndrome, Ormond's disease (tetroperitoneal fibrosis)), perirenal fasciitis, Gerota's fasciitis/syndrome, periureteritis fibrosa, sclerosing lipogranuloma, sclerosing retroperitoneal granuloma, non-specific retroperitoneal inflammation, sclerosing retroperitonitis, retroperitoneal vasculitis with perivascular fibrosis), IgG4-related mesenteritis (subtypes are: mesenteric panniculitis, mesenteric lipodystrophy and retractile mesenteritis) (sclerosing mesenteritis, systemic nodular panniculitis, liposclerosis mesenteritis, mesenteric Weber-Christian disease, mesenteric lipogranuloma, xanthogranulomatous mesenteritis), IgG4-related mastitis (sclerosing mastitis), IgG4-related kidney disease (IgG4-RKD), IgG4-related tubulointerstitial nephritis (IgG4-TIN), IgG4-related membranous glomerulonephritis (idiopathic tubulointerstitial nephritis), IgG4-related prostatitis, IgG4-related perivasal fibrosis (chronic orchialgia), IgG4-related paratesticular pseudotumor, IgG4-related epididymo-orchitis (paratesticular fibrous pseudotumor, inflammatory pseudotumor of the spermatic cord, pseudosarcomatous myofibroblastic proliferations of the spermatic cord, proliferative funiculitis, chronic proliferative periorchitis, fibromatous periorchitis, nodular periorchitis, reactive periorchitis, fibrous mesothelioma), IgG4-related lymphadenopathy, IgG4-related skin disease (angiolymphoid hyperplasia with eosinophilia, cutaneous pseudolymphoma), IgG4-related perineural disease, and IgG4-related thyroid disease (Reidel's thyroiditis), eosinophilic angiocentric fibrosis (affecting the orbits and upper respiratory tract), inflammatory pseudotumour, and multifocal fibrosclerosis. In some embodiments, the disease may be selected from the group consisting of autoimmune pancreatitis (lymphoplasmacytic scleorising pancreatitis), eosinophilic angiocentric fibrosis (affecting the orbits and upper respiratory tract), fibrosing mediastinitis, idiopathic hypertrophic pachymeningitis, idiopathic tubulointerstitial nephritis, inflammatory pseudotumour, Küttner's tumour, Mikulicz's disease, fibrosclerosis, periaortitis, periarteritis, inflammatory aortic multifocal aneurysm, Ormond's disease (tetroperitoneal fibrosis), Riedel's thyroiditis, and sclerosing mesenteritis.

The amount of compound or composition administered to a subject according to the methods of the present invention is, generally, a therapeutically effective amount. As used herein, the phrase therapeutically effective amount means an amount of compound or composition that results in one or more of: (a) an improvement in one or more IgG4-RD associated parameters as assessed by a physician; and/or (b) a detectable improvement in one or more symptoms or indicia of IgG4-RD. A therapeutically effective amount also includes an amount of compound or composition that inhibits, prevents, lessens, or delays the progression of IgG4-RD in a subject.

It has been found that IL-4 inhibitors, for example, IL-4 and IL-13 inhibitors, for example, dupilumab, a commercially available, approved, IL-4 and IL-13 inhibitor which specifically binds to the IL-4Rα subunit of the IL-4 and IL-13 receptor complexes, can be useful in treatment of IgG4-RD. Other IL-4Ra blockers such as Pitrakinra, a 15 kDa human recombinant protein of IL-4, may also be useful in such treatment. Janus Kinase (JAK) Inhibitors which effectively block the effects of IL-4 and IL-13 functions intracellularly may also be useful in such treatment.

As used herein, an "IL-4 receptor alpha (IL-4RA) inhibitor" or "IL-4 receptor alpha (IL-4RA) blocker" is any agent that binds to or interacts with IL-4R and inhibits the normal biological signaling function of IL-4R when IL-4R is expressed on a cell in vitro or in vivo. Non-limiting examples of categories of IL-4R antagonists include small molecule IL-4R antagonists, anti-IL-4R aptamers, peptide-based IL-4R antagonists (e.g., "peptibody" molecules), and antibodies or antigen-binding fragments of antibodies that specifically bind human IL-4R.

Similarly, a compound which blocks assembly of IL-4RA with IL-13 receptor alpha is any agent that disrupts the formation of the IL-4RA and IL-13 receptor alpha complex, or causes the dissociation of the already formed complex, on a cell in vitro or in vivo. This can be through direct binding of the agent to either of the receptors. This compound can also broadly include those agents that inhibit or minimize the biological function of the IL-4RA and IL-13R complex, such as by decreasing downstream signaling. Non-limiting examples of categories of compounds include small molecule antagonists, aptamers, peptide-based antagonists (e.g., "peptibody" molecules), and antibodies or antigen-binding fragments of antibodies.

Dupilumab is an antagonistic monoclonal antibody against human IL-4Ra that inhibits induced biological activities from IL-4 and IL-13. Dupilumab blocks IL-4 signal transduction by preventing its binding to receptor subunits, whereas the inhibitory effect on IL-13 signaling is likely mediated through interfering with the dimeric receptor interaction.

According to certain exemplary embodiments, the methods of the present invention comprise the use of dupilumab, or a bioequivalent thereof. The term "bioequivalent", as used herein, generally refers to anti-IL-4R antibodies or IL-4R-binding proteins or fragments thereof that are pharmaceutical equivalents or pharmaceutical alternatives whose rate and/or extent of absorption do not show a significant difference with that of dupilumab when administered at the same or similar molar dose under similar experimental conditions, either single dose or multiple dose. In the context of the invention, the term refers to antigen-binding proteins that bind to IL-4R which do not have clinically meaningful differences with dupilumab in their safety, purity and/or potency.

Other anti-IL-4Ra antibodies that can be used in the context of the methods of the present invention include, e.g., the antibody referred to and known in the art as AMG317 (Corren et al., 2010, *Am J Respir Crit Care Med.*, 181(8): 788-796), or MEDI 9314, or any of the anti-IL-4Ra antibodies as set forth in U.S. Pat. Nos. 7,186,809, 7,605,237, 7,638,606, 8,092,804, 8,679,487, or U.S. Pat. No. 8,877, 189.

As used herein, a "JAK inhibitor" refers to a compound or a ligand that inhibits at least one activity of a JAK kinase. A "JAK inhibitor" can also be a "JAK1/JAK2 inhibitor", or may include inhibitors of kinases downstream of JAK. In certain embodiments, the JAK inhibitor induces a JAK-inhibited state. JAK inhibitors suitable for human administration are known in the art and include for example, ruxolitinib (INCB018424), CYT-387, TG101348 (SAR302503), AZD1480, lestaurtinib (CEP-701), tofacitinib (CP-690,550), pacritinib (SB1518), baricitinib (LY3009104, INCB28050), BMS-911543, LY2784544, XL019, and NS018.

Pitrakinra (trade name Aerovant) is a 15-kDa human recombinant protein of wild-type human interleukin-4 (IL-4). It is an IL-4 and IL-13 antagonist that blocks the inflammatory effects of IL-4 and IL-13, interrupting the Th2 lymphocyte immune response.

In certain embodiments, the compound or composition is administered to the patient before, after or concurrent with a second therapeutic agent.

A compound or composition, such as dupilumab, may be provided in any effective dose, via any effective administration method. For example, dupilumab may be provided in an initial subcutaneous injection of between 200-1000 mg, for example, 600 mg, followed by periodic follow-on injections, for example, a 200 mg-400 mg subcutaneous injection every other week, a higher dose weekly, twice monthly, bimonthly, monthly, or every other month. The follow-on injections may be continuous, or may be intermittent, for example, by providing a 300 mg subcutaneous injection every other week for 6 months, followed by a one month drug holiday, then resuming treatment. For example, dupilumab may be provided at an initial 600 mg dose, followed by 300 mg ever other week or weekly or monthly or every two months, all subcutaneously. Alternatively, for example, dupilumab may be provided at an initial 400 mg dose, followed by 300 mg every other week or weekly or monthly or every two months, all subcutaneously. Alternatively, for example, dupilumab may be provided at an initial and follow-on dose of 300 mg, every other week, or once every three weeks. Alternative treatment protocols may also be utilized.

Example 1: Treatment of IgG4-RD with Dupilumab

A 67-year-old male with no known allergies and a history of sensory neural hearing loss, recurrent bronchitis, spinal stenosis, moderate positional obstructive sleep apnea, asthma, atopic dermatitis (which caused swelling around his eyes), and allergic rhinoconjunctivitis underwent extensive investigations due to suspected IgG4-RD. The patient's initial complaint was pruritic erythematous lesions on the legs, arms, chest, and palms. Further investigations revealed parotitis, sinusitis, normocytic anemia, and eosinophilia. An MRI showed retroperitoneal and genitourinary fibrosis (FIG. 1a). Total IgG and IgG4 levels were found to be 32.40 g/L and 20.60 g/L, respectively. The patient had a prostate biopsy which revealed 50 IgG4 cells/HPF and an IgG4+/IgG+ cell ratio of 40%. This result was exactly borderline as per the IgG4-RD comprehensive diagnostic criteria [4], making the result of the biopsy probable for IgG4-RD. Interventional radiologists determined the retroperitoneal fibrosis to be inaccessible for biopsy and the patient declined a repeat prostate biopsy. Although the biopsy was borderline, given that the imaging, clinical features, and laboratory investigations fulfilled the remainder of the comprehensive diagnostic criteria (1 to 3a), IgG4-RD was the consensus diagnosis [4].

Laboratory investigations revealed hemoglobin counts of 131 g/L (normal range 135-175 g/L), hematocrit levels of 0.391 L/L (normal range 0.4-0.5 L/L), eosinophil levels of 1.4×E9 cells/liter (normal range 0.0-0.5×E9/L), and alkaline phosphatase serum levels of 34 U/L (normal range 40-129 U/L). Upon examination, signs consistent with atopic dermatitis was present with 50% body surface area (BSA) involvement with an Investigator Global Assessment (IGA) score of 4, indicating severe disease. An initial 600 mg subcutaneous injection of dupilumab, followed by a 300 mg subcutaneous injection every other week for twelve months was given to treat atopic dermatitis, asthma, and IgG4-RD.

Figure 1B:
FIG. 1b shows a patient's post-treatment MRI, showing dramatic resolution of fibrosis.

After 3 months on dupilumab, the patient's eye swelling resolved, and his skin and asthma noticeably improved to IGA1 and <10% BSA. Both total IgG and IgG4 levels reduced substantially to 19.41 g/L and IgG4 levels of 11.43 g/L, respectively. After 12 months on dupilumab, the patient's retroperitoneal fibrosis improved dramatically corresponding with the decreased IgG4 levels (FIG. 1b). In this patient, IgG4-RD was controlled with no further relapses across all affected organ systems with no significant long-term adverse events with an additional 9 months from original publication in Ann Rheum Dis. 2020 April; 79(4): 549-550 of follow up recorded since original publication while remaining on dupilumab.

The invention claimed is:

1. Method of treating IgG4-Related Disease (RD) selected from the group consisting of IgG4-associated asthma, atopic dermatitis, organ sclerosis (including sclerosing pancreatitis), cholangitis, and organ fibrosis, in a patient in need thereof comprising administering an effective amount of dupilumab or a pharmaceutically acceptable salt thereof, wherein the IgG4-Related Disease is treated or the effects of the disease are diminished by said effective amount.

2. The method of claim 1 wherein the administration is via a subcutaneous injection.

3. The method of claim 1 wherein the administration is oral.

4. The method of claim 1 wherein the administration is a parenteral administration.

5. The method of claim 1 wherein the effective amount is an initial dose of 600 mg followed by a 300 mg dose every other week, or an initial dose of 400 mg followed by a 200 mg dose every other week.

* * * * *